(12) United States Patent
Popovich

(10) Patent No.: US 6,356,366 B1
(45) Date of Patent: Mar. 12, 2002

(54) HOLOGRAPHIC LIGHT FOCUSING DEVICE

(75) Inventor: Milan M. Popovich, Leicester (GB)

(73) Assignee: Digilens, Inc., Sunnyvale, CA (US)

( * ) Notice: Subject to any disclaimer, the term of this patent is extended or adjusted under 35 U.S.C. 154(b) by 0 days.

(21) Appl. No.: 09/692,506

(22) Filed: Oct. 18, 2000

Related U.S. Application Data
(60) Provisional application No. 60/160,794, filed on Oct. 21, 1999.

(51) Int. Cl.$^7$ .................................................. G02B 5/32
(52) U.S. Cl. ........................... 359/15; 359/22; 359/34; 606/17
(58) Field of Search ............................... 359/1, 15, 22, 359/34; 607/15–17

(56) References Cited

U.S. PATENT DOCUMENTS

| | | | |
|---|---|---|---|
| 5,063,379 A | 11/1991 | Fabry et al. | 340/784 |
| 5,506,701 A | 4/1996 | Ichikawa | 359/15 |
| 5,680,231 A | 10/1997 | Grinberg et al. | 359/15 |
| 5,751,452 A * | 5/1998 | Tanaka et al. | 349/33 |
| 5,768,242 A * | 6/1998 | Juday | 369/94 |
| 5,844,709 A | 12/1998 | Rabinovich et al. | 359/248 |
| 5,868,480 A | 2/1999 | Zeinali | 353/31 |

* cited by examiner

*Primary Examiner*—Darren Schuberg
(74) *Attorney, Agent, or Firm*—Van Pelt & Yi LLP

(57) ABSTRACT

A holographic light focusing device is disclosed. The device generally comprises an elongate member having an input end and an output end, a light source disposed at the input end, and a light guide extending along the elongate member and operable to guide a light beam emitted from the light source to the output end of the elongate member. The device further comprises a focusing system disposed at the output end of the elongate member. The focusing system includes a plurality of holographic optical elements switchable between an active state wherein light from the light source is diffracted by the element to focus the light and a passive state wherein the light is not substantially diffracted by the device. Each of the holographic elements is configured to focus the light at a different distance relative the output end when in its active state.

21 Claims, 2 Drawing Sheets

HOLOGRAPHIC LIGHT FOCUSING DEVICE

RELATED APPLICATIONS

The present application claims the benefit of U.S. Provisional Application Serial No. 60/160,794, filed Oct. 21, 1999.

BACKGROUND OF THE INVENTION

The present invention relates generally to holographic devices, and more particularly, to laser devices such as those employed in microsurgery.

Surgery which is conducted by the insertion of instruments through relatively small incisions in the body often requires that illumination be introduced into the body. It is desirable to have the light source associated with a surgical instrument which will be used in the surgery since this limits the number of incisions that have to be made. In addition to the light source, an imaging device is often needed so that a surgeon can see the area he is working on to explore within the open cavity. The small size of the operating space makes it desirable to limit the number of separate instruments used at the same time in the operating space. Thus, the more functions a single surgical instrument can perform the better, so long as the size of the instrument remains small.

Furthermore, it is often desirable to focus a light source such as a laser within the confined operating space. Conventional optical focusing devices are typically bulky and cannot easily be mounted on a compact surgical tool.

SUMMARY OF THE INVENTION

A holographic light focusing device is disclosed. The device generally comprises an elongate member having an input end and an output end, a light source disposed at the input end, and a light guide extending along the elongate member and operable to guide a light beam emitted from the light source to the output end of the elongate member. The device further comprises a focusing system disposed at the output end of the elongate member. The focusing system includes a plurality of holographic optical elements switchable between an active state wherein light from the light source is diffracted by the element to focus the light and a passive state wherein the light is not substantially diffracted by the device. Each of the holographic elements is configured to focus the light at a different distance relative to the output end when in its active state.

In another aspect of the invention a surgical instrument generally comprises a flexible elongate member sized for insertion through the outer envelope of a living body for surgical operation within the body and has an input end and an output end. The instrument further includes a light guide extending along the elongate member and comprising a plurality of light conducting fibers operable to guide a light beam emitted from a light source from the input end to the output end of the elongate member. A focusing system is disposed at the output end of the elongate member and comprises a plurality of holographic optical elements switchable between an active state wherein light from the light source is diffracted by the element to focus the light and a passive state wherein the light is not substantially diffracted by the device. Each of the holographic elements is configured to focus the light at a different location relative to the Output end when in its active state.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE INVENTION

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
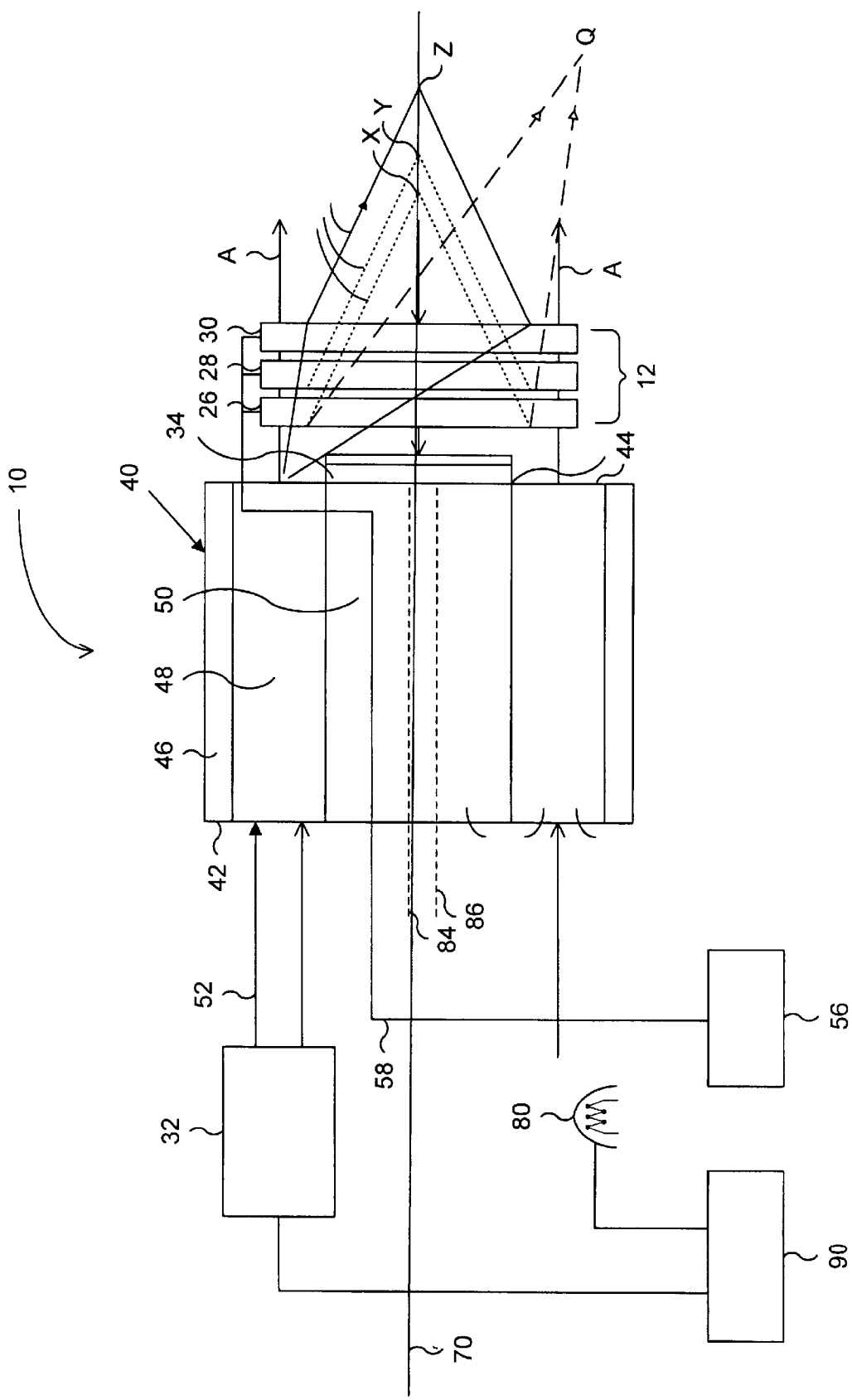
FIG. 1 is schematic of a holographic light focusing device of the present invention.

Referring now to the drawings, and first to FIG. 1, a holographic light focusing device of the present invention is shown, and generally indicated at 10. The device 10 may be used, for example, for microsurgery or laser microsurgery so that a laser beam can be targeted on a specific area. The device 10 includes a focusing system used to focus a laser beam on a specific area to cauterize a vessel or ablate certain tissue in the body, for example. The focusing system includes a plurality of holographic optical elements 26, 28, 30 that are used to focus a laser 32 at different locations. The use of holographic optical elements 26, 28, 30 enables the light focusing system 12 to be compact, which is important in applications such as microsurgery, where the device is used in very small confined spaces. An outer diameter of the device 10 is preferably sized for insertion through a small incision in the outer envelope of a living body for surgical operation within the body. The device 10 further includes an illumination system operable to illuminate an area adjacent to an output end of the device and a detector 34 so that an image of the area can be viewed by a surgeon. It is to be understood that the device 10 may be used in applications other than microsurgery, without departing from the scope of the invention. For example, the device may be used for engine inspection, process monitoring and diagnostics, and welding. The device may form part of a robotic system for performing these or other functions. Another possible application is in flow measurement where light scattered back from molecules or tracer particles transversing one or more laser focal spots can provide information on fluid velocity. This can be accomplished by measuring the time interval between signals from laser focal spots of known separation, or alternatively, by measuring the change in frequency of the back scattered light as in Laser Doppler anemometry technique, for example.

In one embodiment the device 10 is in the form of an endoscope and comprises an elongate member, generally indicated at 40, of which only a portion is shown. The elongate member 40 is preferably flexible to allow for movement of the instrument through narrow passages. The elongate member 40 includes an input end 42 and an output end 44 and comprises an outer sheath or cladding layer 46, a light transmitting ring 48 and a central core 50. The outer sheath 46 may be made of silicone, plastic, or other suitable material that is sufficiently flexible. The light transmitting ring 48 comprises fibers made of plastic, quartz, glass, silica, or any other suitable light conducting material. The input end 42 of the elongate member 40 preferably includes a grip (not shown) sized so that a surgeon may hold the device in one hand and manipulate the elongate member.

Laser light source 32 is disposed at the input end 42 of the elongate member 40. The light transmitting core 48 acts as a light guide to transmit a laser beam 52 from the source 32 to the output end 44 of the member elongate. Focusing system 12 is disposed at the output end 44 of the elongate member 40 to focus the laser beam 52 at a specific location. The focusing system 12 includes a stack of holographic optical elements 26, 28, 30. Each element 26, 28, 30 effectively acts as a lens and has a predetermined optical power. The holographic optical elements 26, 28, 30 are each independently switchable between an active, focusing state and an inactive (passive), non-focusing state under the operation of a controller 56. Cable 58 connects the holographic optical elements 26, 28, 30 to the controller 56 and passes through the central core 50 of the elongate member 40. Many different types of lasers may be used depending on the application. Flourescence measurements would typically require ultraviolet or blue lasers. The laser may be based on solid state technology such as a neodymium YAG emitting in the near infrared or may be a gas laser using astrology or krypton gas emitting, in the visible band, for example. For surgical applications, low power lasers with powers measured in milliwatts are typically used. Some applications such as welding and laser anemometry may require high power, typically measured in watts.

Figure 2:
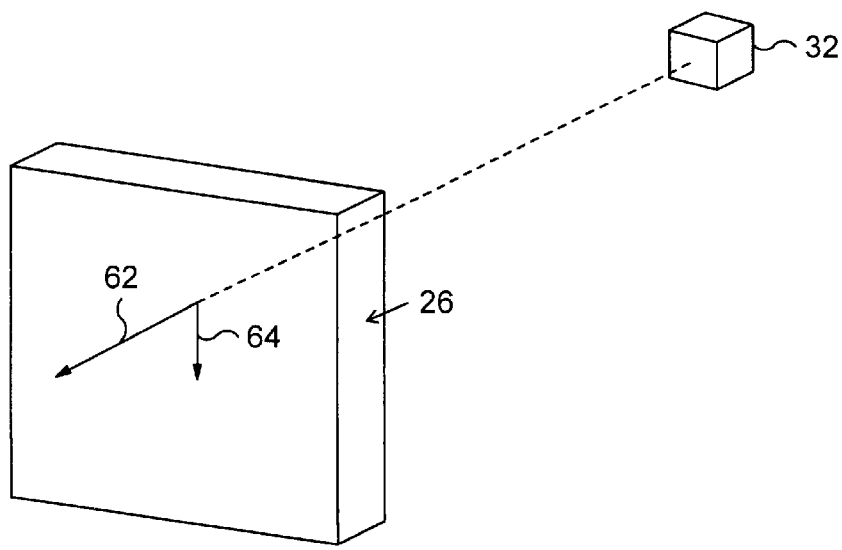
FIG. 2 is a perspective view of a holographic optical element and light source of the holographic device of FIG. 1.
Figure 3:
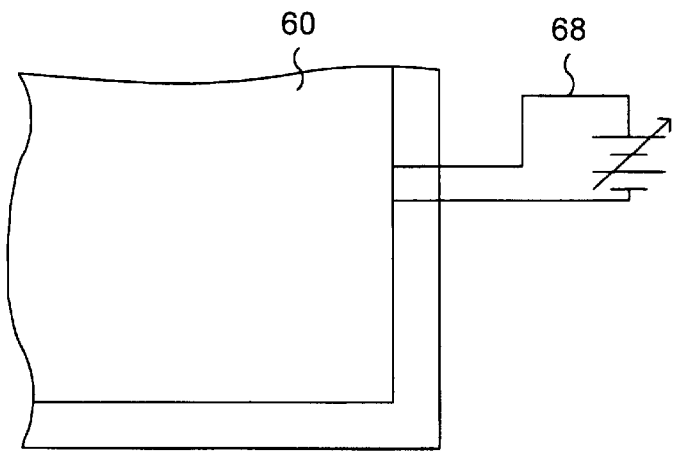
FIG. 3 is a partial front view of the holographic optical element of FIG. 2 illustrating electrode and electric circuit of the holographic optical clement.

The holographic optical elements 26, 28, 30 each include a hologram interposed between two electrodes 60 (FIGS. 2 and 3). The hologram may be a Bragg (thick or volume) hologram or Raman-Nath (thin) hologram. Raman-Nath holograms are thinner and require less voltage to switch light between various modes of the hologram, however, Raman-Nath holograms are not as efficient as Bragg holograms. The Bragg holograms provide high diffraction efficiencies for incident beams with wavelengths close to the theoretical wavelength satisfying the Bragg diffraction condition and within a few degrees of the theoretical angle which also satisfies the Bragg diffraction condition.

The hologram is used to control transmitted light beams based on the principles of diffraction. The hologram selectively directs an incoming light beam from the light source 32 either towards or away from a viewer and selectively diffracts light at certain wavelengths into different modes in response to a voltage applied to the electrodes 60. Light passing through the hologram in the same direction as the light is received from the light source 32 is referred to as the zeroth (0th) order mode 62 (FIG. 2). When no voltage is applied to the electrodes 60, liquid crystal droplets within the holographic optical element 26, 28, 30 are oriented such that the hologram is present in the element and light is diffracted from the zeroth order mode to a first (1st) order mode 64 of the hologram. When a voltage is applied to the holographic optical clement 26, 28, 30, the liquid crystal droplets become realigned effectively erasing the hologram, and the incoming light passes through the holographic optical element in the zeroth order mode 62.

The light that passes through the hologram is diffracted by interference fringes recorded in the hologram. Depending on the recording, the hologram is able to perform various optical functions which are associated with traditional optical elements, such as lenses and prisms, as well as more sophisticated optical operations. The hologram may be configured to perform operations such as deflection or focusing of the light, for example.

The holograms are preferably recorded on a photopolymer/liquid crystal composite material (emulsion) such as a holographic photopolymeric film which has been combined with liquid crystal, for example. The presence of the liquid crystal allows the hologram to exhibit optical characteristics which are dependent on an applied electrical field. The photopolymeric film may be composed of a polymerizable monomer having dipentaerythritol hydroxypentacrylate, as described in PCT Publication, application No. PCT/US97/12577, by Sutherland et al., which is incorporated herein by reference in its entirety. The liquid crystal may be suffused into the pores of the photopolymeric film and may include a surfactant.

The diffractive properties of the holographic optical elements 26, 28, 30 depend primarily on the recorded holographic fringes in the photopolymeric film. The interference fringes may be created by applying beams of light to the photopolymeric film. Alternatively, the interference fringes may be artificially created by using highly accurate laser writing devices or other replication techniques, as is well known by those skilled in the art. The holographic fringes may be recorded in the photopolymeric film either prior to or after the photopolymeric film is combined with the liquid crystal. In the preferred embodiment, the photopolymeric material is combined with the liquid crystal prior to the recording. In this preferred embodiment, the liquid crystal and the polymer material are pre-mixed and the phase separation takes place during the recording of the hologram, such that the holographic fringes become populated with a high concentration of liquid crystal droplets. This process can be regarded as a dry "process", which is advantageous in terms of mass production of the switchable holographic optical elements. As further described below, the optical properties of the holographic optical elements 26, 28, 30 primarily depend on the recorded holographic fringes in the photopolymeric film.

The electrodes (electrode layers) 60 are positioned on opposite sides of the emulsion and are preferably transparent so that they do not interfere with light passing through the hologram (FIG. 3). The electrodes 60 may be formed from a vapor deposition of Indium Tin Oxide (ITO) which typically has a transmission efficiency of greater than 80%, or any other suitable substantially transparent conducting material. The transmission may be increased to above 98% by adding suitable antireflection coatings to the electrodes. The electrodes 60 are connected to an electric circuit 68 operable to apply a voltage to the electrodes, to generate an electric field. Initially, with no voltage applied to the electrodes 60, the hologram is in the diffractive (active) state and the holographic optical element 26, 28, 30 diffracts propagating light in a predefined manner. When an electrical field is generated in the hologram by applying a voltage to the electrodes 60 of the holographic optical element 26, 28, 30 the operating state of the hologram switches from the active state to the passive state and the holographic optical element does not optically alter the propagating light. It is to be understood that the electrodes may be different than described herein. For example, a plurality of smaller electrodes may be used rather than two large electrodes which substantially cover surfaces of the holograms.

The controller 56 drives switching circuitry 68 associated with the electrodes 60 on each of the optical elements 26, 28, 30 to apply a voltage to the electrodes (FIGS. 3 and 4). The electrodes 60 are individually coupled to the controller 56 through a voltage controller (not shown) which selectively provides an excitation signal to the electrodes 62 of a selected holographic optical element 26, 28, 30, switching the hologram to the passive state. The voltage controller also determines the specific voltage level to be applied to each electrode 60. A voltage may be applied across the hologram such that the holographic optical element 26, 28, 30 is in a partially active state in which light passing through the hologram is partially affected by the optical characteristics of the hologram.

Each holographic optical element 26, 28, 30 is holographically configured to focus the laser beam 52 at a point which is a different distance from the output end 44 of the elongate member 40. When the holographic optical element 26 is activated, it operates to focus the light at point X. Holographic optical element 28 focuses the light at point Y when it is activated. When holographic optical element 30 is activated, it focuses the laser light at point Z. Thus, by selectively switching between the various holographic optical elements 26, 28, 30, the laser beam can be focused at different points. As shown in FIG. 1, each point X, Y, Z is located generally along a central longitudinal axis 70 of the elongate member 40. One or more of the holographic optical elements 26, 28, 30 may also be configured to focus the laser beam 52 off-axis at point Q (as indicated by dashed lines).

Preferably, only one pair of electrodes 60 associated with one of the three holographic optical elements 26, 28, 30 is energized at one time. For example, when the light is to be focused at point X, the controller 56 switches the holograms 28, 30 to their passive state by applying voltages to their respective electrodes 60. The supplied voltages to the electrodes 60 of the holograms 28, 30 create a potential difference between the electrodes, thereby generating an electrical field within the holograms. The presence of the electrical field switches the optical characteristics of the holograms 28, 30 to the passive state. With the holograms 28, 30 in their passive state and the hologram 26 in its diffractive state, only hologram 26 optically diffracts the laser beam. Similarly, a voltage is applied to the electrodes of holographic optical elements 26, 30 to focus the light at point Y, and a voltage is applied to elements 26, 28 and removed from element 30 to focus the light at point Z. The holographic optical elements 26, 28, 30 may be switched at a rate less than 150 microseconds, for example.

The focusing system 12 may include additional optical components. For example, cylindrical, prismatic, or off-axis aspheric optical components (not shown) may also be included in the focusing system 12 to correct for geometric aberrations, as is well known by those skilled in the art. These components would typically be required for off axis focusing as in the case of point Q of FIG. 1, for example.

A light source 80, such as a incoherent light source may be disposed at the input end 44 of the elongate member 40. The light source 80 may also be another energy source, such as an ultraviolet light. The light transmitting member 48 operates as a light guide to transmit light from the light source 80 to the output end 44 of the elongate member 40, as previously described for the laser beam 52. As indicated by arrows A, light exits the output end 44 of the elongate member 40 and illuminates an object or area to be inspected. Radiation sensitive detector 34 is mounted on the output end 44 of the elongate member 40. The detector 34 is preferably sized so as not to obstruct the emission of light from the light transmitting member 48. Signals from the detector 34 pass along line 84 to the input end 42 of the elongate member 40. The signals are then processed into an image. Line 84 is preferably located within the central core 50 of the elongate member 40, along with a drive line 86 coupled to the detector 34. The detector 34 may include a photodetector comprising a plurality of detector elements (e.g., charge-coupled detectors (CCDs), photo capacitors, photo resistors, photo diodes, or any other suitable light-sensitive device). The detector 34 may also be a fluorescent detector operable to detect cancer cells or other abnormalities. The detector 34 may be equipped with a lens or lens array either for the purpose of forming an image at the surface of the detector, or in the case when the detector is not being used for imaging, to concentrate as much light as possible onto the surface of the detector. The detector 34 may communicate with a display (not shown) for direct viewing of the image, or the image may be captured on film or stored in a computer. The detector 34 may be configured to operate in fill color (e.g., visible red, green, and blue light). A light controller 90 may be provided to energize the light source 80 and the laser light source 32. The light controller 90 is preferably coupled to the focusing system controller 56 so that the focusing controller deactivates all of the holographic optical elements 26, 28, 30 when the light controller 90 energizes the white light source. This allows the device 10 to be operated in two different operating modes. In the first mode, the device 10 is used for laser operation by energizing the laser light source 32 and activating the appropriate holographic optical element 26, 28, 30. In the second mode of operation, the device 10 is used for inspection purposes, with the area inspected being illuminated by light from white light source 80 and an image of the inspected area being formed by the detector 34. In this second mode, light back-scattered from the area being inspected passes straight through the holographic optical elements 26, 28, 30 which are deactivated and have no appreciable effect on the light.

Although the present invention has been described in accordance with the embodiments shown, one of ordinary skill in the art will readily recognize that there could be variations made to the embodiments without departing from the scope of the present invention. Accordingly, it is intended that all matter contained in the above description and shown in the accompanying drawings shall be interpreted as illustrative and not in a limiting sense.

What is claimed is:

1. A holographic light focusing device comprising:
   an elongate member having an input end and an output end;
   a light source disposed at said input end;
   a light guide extending along said elongate member and operable to guide a laser beam emitted from said light source to said output end of said elongate member; and
   a focusing system disposed at said output end of the elongate member and comprising a plurality of holographic optical elements switchable between an active state wherein light from the light source is diffracted by the element to focus said light and a passive state wherein said light is not substantially diffracted by the device; each of the holographic elements configured to focus the light at a different position relative to the output end when in its active state.

2. The device of claim 1 wherein the holographic optical elements each include a hologram interposed between two electrode layers operable to apply an electrical field to the hologram.

3. The device of claim 2 wherein the hologram is formed from a polymer and liquid crystal material.

4. The device of claim 1 wherein each of the holographic optical elements has a hologram recorded therein to focus light at a different distance from the output end of the elongate member.

5. The device of claim 4 wherein at least one of the holograms is configured to focus light generally along a central longitudinal axis of the elongate member.

6. The device of claim 4 wherein at least one of the holograms is configured to focus light spaced laterally from the central longitudinal axis of the elongate member.

7. The device of claim 4 wherein each of the holograms is interposed between two electrode layers operable to apply an electrical field to the hologram.

8. The device of claim 7 further comprising a controller operable to sequentially supply voltage to and remove voltage from the electrode layers of each holographic optical element.

9. The device of claim 1 wherein said plurality of holographic optical elements comprises three holographic optical elements.

10. The device is claim 1 wherein the light source is a laser.

11. The device of claim 1 further comprising an illumination system operable to illuminate an area located adjacent to the output end of the elongate member.

12. The device of claim 11 wherein the illumination system comprises a white light source.

13. The device of claim 11 wherein the illumination system comprises an ultraviolet light source.

14. The device of claim 11 further comprising a light detector.

15. The device of claim 14 wherein the light detector is operable to transmit an image of the illuminated area from the output end of the elongate member to the input end.

16. The device of claim 14 wherein the detector is a CCD.

17. The device of claim 11 further comprising an illumination controller operable to switch the illumination system on generally simultaneously with the holographic optical elements being switched to their passive states.

18. A surgical instrument comprising:
   a flexible elongate member sized for insertion through the outer envelope of a living body for surgical operation within the body and having an input end and an output end;
   a light guide extending along said elongate member and comprising a plurality of light conducting fibers operable to guide a light beam emitted from a light source from said input end to said output end of said elongate member; and
   a focusing system disposed at said output end of the elongate member and comprising a plurality of holographic optical elements switchable between an active state wherein light from the light source is diffracted by the element to focus said light and a passive state wherein said light is not substantially diffracted by the device; each of the holographic elements configured to focus the light at a different distance relative to the output end when in its active state.

19. The instrument of claim 18 further comprising a laser light source disposed at said input end.

20. The instrument of claim 18 further comprising an image transmitting system operable to transmit an image located generally at said output end of the elongate member to said input end of the elongate member.

21. The instrument of claim 20 wherein the image transmitting system includes an incoherent light source disposed at said input end of the elongate member.

* * * * *